United States Patent [19]

Van Sickle

[11] Patent Number: 4,484,011

[45] Date of Patent: Nov. 20, 1984

[54] PROCESS FOR PREPARATION OF 4-ISOPROPYLPHENOL

[75] Inventor: Dale E. Van Sickle, Kingsport, Tenn.

[73] Assignee: Eastman Kodak Company, Rochester, N.Y.

[21] Appl. No.: 557,691

[22] Filed: Dec. 2, 1983

[51] Int. Cl.³ .................... C07C 37/48; C07C 39/06
[52] U.S. Cl. ................................. 568/781; 568/716; 568/783; 568/790; 568/791; 568/793; 568/794
[58] Field of Search ............... 568/716, 781, 780, 783, 568/788, 786, 789, 790, 791, 793, 794

[56] References Cited

U.S. PATENT DOCUMENTS

| | | | |
|---|---|---|---|
| 2,286,953 | 6/1942 | Scott | 568/781 |
| 3,839,470 | 10/1974 | Biller | 568/781 |
| 3,933,927 | 1/1976 | Goodard | 568/781 |
| 4,200,763 | 4/1980 | Dai | 560/109 |
| 4,339,614 | 7/1982 | Olah | 568/768 |
| 4,423,254 | 12/1983 | Olah | 568/781 |

FOREIGN PATENT DOCUMENTS 141226 12/1978 Japan ........................ 568/781

*Primary Examiner*—Werren B. Lone
*Attorney, Agent, or Firm*—Donald W. Spurrell; Daniel B. Reece, III

[57] ABSTRACT

The process for preparing 4-isopropylphenol (4-IPP) from 2-isopropylphenol (2-IPP) comprising contacting phenol with 2-IPP in the presence of a catalyst system selected from: (1) the combination of sulfuric acid on comminuted acid clay and a molecular sieve; and (2) trifluoromethane sulfonic acid (TFMSA); at a temperature of from about 90° C. to about 250° C., preferably from about 110° C. to about 200° C., wherein the initial mole ratio of phenol/2-IPP is from about 6 to about 2, preferably from about 4 to about 2.5, for a sufficient period to give a mole ratio of 4-IPP/2-IPP in the reaction system of from about 0.6 to about 1.5, and preferably from about 0.8 to about 1.2, without significant meta-isopropylphenol formation, i.e., less than about 10 mole %. In the isolation procedure, distillation separates the reaction mixture into phenol, 2-IPP, and 4-IPP.

8 Claims, No Drawings

PROCESS FOR PREPARATION OF 4-ISOPROPYLPHENOL

This invention concerns the preparation of 4-isopropylphenol (4-IPP) by the transalkylation of 2-isopropylphenol (2-IPP).

The 4-isopropylphenol is typically manufactured by isopropylation of phenol which gives generally isomeric mixtures of ortho- and para-isopropylphenol. The proportion of the para-isomer is minor, usually about 30–40 mole % or less, and thus the economics of the process is quite poor. Attempts to rectify this situation, using for example, the known acid catalyzed isomerization technology with Friedel-Crafts catalysts such as $AlCl_3$, $BF_3$, and the like in the liquid phase, or over solid catalysts such as Nafion-H and PDSA, typically gives isomer distributions of about 15% ortho-, 65% meta- and 20% para- which requires expensive and difficult distillation procedures for separating the isomers. The very close boiling range of the meta- and para-isomers, for example, renders isomer separation very difficult. A more detailed review of the alkylation of phenol with propylene, and the resulting isomeric mixtures is found in Chem. Ing. Tech. 53 (1981) Nr. 12, S. 954–957.

The present invention has as its object therefore, to provide a method for markedly improving the overall economics of 4-IPP production by converting the ortho-isomer (2-IPP) to the para-isomer (4-IPP) in relatively high yield at nominal energy input and without significant attendant meta-isomer formation. The 4-IPP is useful, for example, in the manufacture of hydroquinone by the autoxidation of the isopropylphenyl ester as taught in U.S. Pat. No. 4,200,763.

This object has been achieved in accordance with the present invention through the discovery that certain specific catalyst systems can transalkylate phenol with 2-IPP at relatively low temperatures to give a reaction system high in, if not predominately, the 4-IPP isomer. In this process, a very acceptable ratio of 4-IPP/2-IPP can be achieved before a significant concentration of meta-isopropylphenol is formed.

As indicated above, it is known in the art to isomerize various isopropylphenol isomer mixtures as discussed, for example, in U.S. Pat. No. 4,339,614, to give a higher yield of a particular isomer, but such technology is silent on improving the production of 4-IPP. In that patent it is noted that when isopropylphenol isomer mixtures were treated in excess anhydrous hydrogen fluoride with a Lewis acid fluoride at +50° C. to 200° C., substantially complete conversion to the meta-isomer occurred, accompanied by some disproportionation to phenol and diisopropylphenols. It is also noted therein that superacid systems form protonated complexes with isopropyl phenols of which the one derived from the meta-isomer is the most stable. Thus, the superacid systems tend to selectively extract the meta-isomer and allow a selective conversion of all isomers to the meta-product.

Isomerization experiments on 2-IPP have been reported also by G. Bertholon and R. Perrin, Bull. Soc. Chim. Fr., 1975, 1537, wherein pure or nearly pure 2-IPP was subjected to acidic conditions. Pure 2-IPP disproportionated and yielded substantial quantities of phenol and diisopropylphenols as well as 3- and 4-IPP when dissolved in phosphoric acid and held at 200° C. The "superacid" system $HF-BF_3$ at 110° C. yielded 61% 3-IPP and, presumably, 39% of mixed phenol and polyisopropylphenols as reported in U.S. Pat. No. 4,339,614.

Relative to the t-butyl group, the isopropyl group appears quite inert to transalkylation to another aromatic nucleus and substantial time was spent investigating acid catalysts which turned out to be ineffective. Such catalysts included p-toluenesolfonic acid (monohydrate), methanesulfonic acid (98%), 10% phosphoric acid on "KSF" clay, 10% sulfuric acid on "KSF" clay (in the absence of SK 500 molecular sieves) and the molecular sieve SK 500 alone. Temperatures up to 190° C., the approximate reflux temperature of the phenol-/isopropylphenol mixture, were investigated. With the exception of the "superacid" trifluoromethanesulfonic acid, acidic cataysts which were effective were used in conjunction with the molecular sieves, a fact which suggested that the drying action of the sieves was a critical factor. However, a mixture of phenol/isopropylphenol dried with 3A molecular sieves suspended in a screen basket which was removed prior to the addition of 10% sulfuric acid on KSF clay did not isomerize.

Experiments carried out during my investigations indicated that isomerization of 2-IPP requires relatively harsh conditions and that disproportionation to form dialkylphenols and phenol is a serious competing reaction.

Such investigative results emphasizes the unobviousness of the present process which unexpectedly produces high yields of the 4-IPP. The present process comprises contacting phenol with 2-IPP in the presence of: (1) from about 1/20 to about 2/1, preferably from about 1/6 to about 1/1 parts per part of 2-IPP of a catalyst comprising the combination of (a) sulfuric acid treated comminuted acid clay having a $H_2SO_4$ concentration of from about 2% to about 40% by weight of the clay, preferably from about 5% to about 20%, and (b) a molecular sieve in a parts by weight ratio of from about 10/1 to about 1/10, preferably from about 5/1 to about 1/5 of (a)/(b); or in the presence of (2) from about 1/20 to about 1/1, preferably from about 1/10 to about 1/5 parts per part of 2-IPP of trifluoromethane sulfonic acid (TFMSA); at a temperature of from about 90° C. to about 250° C., preferably from about 110° C. to about 200° C., wherein the initial mole ratio of phenol/2-IPP is from about 6 to about 2, preferably from about 4 to about 2.5, for a sufficient period to give a mole ratio of 4-IPP/2-IPP in the reaction system of from about 0.6 to about 1.5, and preferably from about 0.8 to about 1.2, without significant meta-isopropylphenol formation, i.e., less than about 10 and preferably less than about 5 mole %. In the isolation procedure, distillation separates the reaction mixture into phenol, 2-IPP, and 4-IPP. If TFMSA is used as the isomerization catalyst it distills before or with the unchanged phenol. The phenol and 2-IPP are returned to the isomerization reactor and the 4-IPP is added to the product stream.

More specifically, the first above catalyst system for effecting this isomerization, preferably is the combination of 10% sulfuric acid adsorbed on a montmorillonite clay and a molecular sieve, specifically the one designated SKF 500 by Union Carbide Corporation. Neither material working separately is effective. Thus, for this catalyst system, 12.5 g. of 2-IPP, 37.5 g. of phenol and 2.0 g. of the SKF 500 molecular sieve were stirred for one hour at the reflux (190° C.). Then 2.0 g. of the sulfuric acid-on-clay catalyst were added and the stirring at reflux was continued. Intermediate samples were taken, but by the time 600 minutes had elapsed, the mixture analyzed as 10.3% 4-IPP, 13.2% 2-IPP, 73.8% phenol and 1.7% 3-IPP along with 0.9% high boiling product. Separation of the 2-IPP from the 4-IPP is readily achieved by fractional distillation. The trifluoromethane sulfonic acid is a much more active catalyst and the same phenol/2-IPP mixture in the presence of this catalyst gave 16.8% 4-IPP, 11.4% 2-IPP, 0.8% 3-IPP and 1.8% high boilers in 250 minutes at 125° C.

The useful acid clays include montmorillomite, bentonite, Fuller's earth and kieselguhr, or any of the solid acidic oxide mixtures of silica and alumina wherein the oxides can be present in any proportion. The weight ratio of preferred $SiO_2/Al_2O_3$ mixed oxides are within the range of from about 90:10 to about 70:30. The clays should provide surface areas in the range of from about 20 to about 250 $M^2/g$. The $H_2SO_4$ is adsorbed on the clay particles by slurrying the particles in diluted $H_2SO_4$ and then evaporating the water.

The useful molecular sieves are the high surface area (> about 400 $M^2/g$) catalysts comprised of various combinations of $SiO_2$, $Al_2O_3$, $Na_2O$ and $Re_2O_3$ typified by the Linde Molecular Sieve Catalyst SK-500 containing, in approximate % by weight, 65% $SiO_2$, 22.7% $Al_2O_3$, 1.6% $Na_2O$ and 10.7% $Re_2O_3$.

The reaction may be carried out as a batch operation, e.g., in a stirred reactor with reflux condenser, wherein the isomers are separated by distillation after analysis of the reaction system shows the desired 4-IPP/2-IPP mole ratio. Alternatively, the reaction can be carried out in continuous fashion by mixing the reactant phenols with a slurry of the clay and molecular sieve powders in a continuous stirred tank reactor (CSTR). Residence times and reactor temperatures are selected to give the desired degree of conversion of the 2-IPP. Reaction temperatures in the range 120°–220° C. and residence times in the range 100 to 500 minutes are suitable. The output stream from the continuous reactor is directed to a settling basin wherein the concentrated catalyst slurry at the bottom is pumped back to the reactor while the clear supernatant is conveyed to a distillation train for separation of product 4-IPP from unreacted 2-IPP and phenol, which reactants are then recycled. For the case where TFMSA is utilized as catalyst, direct distillation of the CSTR effluent produces the recycle and product streams, i.e., the reactants TFMSA, phenol and 2-IPP, and 4-IPP respectively.

During the transalkylation, the ortho-, meta-, and para-isomer concentrations are monitored by gas chromatography, and when a target para-/ortho-ratio is achieved, or when a significant meta-isomer concentration starts to occur, the system temperature is reduced to ambient, the solid catalyst removed by filtration and the product mixture subjected to distillaton.

The invention has been described in detail with particular reference to preferred embodiments thereof, but it will be understood that variations and modifications can be effected within the spirit and scope of the invention.

I claim:

1. The process for preparing 4-isopropylphenol (4-IPP) comprising contacting phenol with 2-isopropylphenol (2-IPP) in the presence of: (1) from about 1/20 to about 2/1 parts per part of 2-IPP of a catalyst comprising the combination of (a) sulfuric acid treated comminuted acid clay having a $H_2SO_4$ concentration of from about 2% to about 40% by weight of the clay, and (b) a molecular sieve in a parts by weight ratio of from about 10/1 to about 1/10 of (a)/(b); or in the presence of (2) from about 1/20 to about 1/1 parts per part of 2-IPP of trifluoromethane sulfonic acid (TFMSA); at a temperature of from about 90° C. to about 250° C., wherein the initial mole ratio of phenol/2-IPP is from about 6 to about 2, for a sufficient period to give a mole ratio of 4-IPP/2-IPP in the reaction system of from about 0.6 to about 1.5 without significant meta-isopropylphenol formation.

2. The process of claim 1 comprising contacting phenol with 2-IPP in the presence of: (1) from about 1/6 to about 1/1 parts per part of 2-IPP of a catalyst comprising the combination of (a) sulfuric acid treated comminuted acid clay having a $H_2SO_4$ concentration of from about 5% to about 20% by weight of the clay, and (b) a molecular sieve in a parts by weight ratio of from about 5/1 to about 1/5 of f(a)/(b); or (2) from about 1/10 to about 1/5 parts per part of 2-IPP of trifluoromethane sulfonic acid (TFMSA); at a temperature of from about 110° C. to about 200° C., wherein the initial mole ratio of phenol/2-IPP is from about 4 to about 2.5, for a sufficient period to give a mole ratio of 4-IPP/2-IPP in the reaction system of from about 0.8 to about 1.2, with less than about 5 mole % meta-isopropylphenol formation.

3. The process of claim 1 wherein the clay is selected from one or more of montmorillonite, bentonite, Fuller's earth, kieselguhr, and the solid acidic oxide mixtures of silica and alumina, wherein the clay has a surface area from about 20 to about 250 $M^2/g$.

4. The process of claim 3 wherein the molecular sieve is selected from one or more of those having a surface area of greater than about 400 $M^2/g$, and being comprised of combinations of $SiO_2$, $Al_2O_3$, $Na_2O$ and $Re_2O_3$.

5. The process of claim 4 wherein the molecular sieve contains, in approximate % by weight, 65% $SiO_2$, 22.7% $Al_2O_3$, 1.6% $Na_2O$ and 10.7% $Re_2O_3$.

6. The process in claim 1 wherein the catalyst is trifluoromethane sulfonic acid in a concentration of from about 1/10 to about 1/5 parts per part of 2-IPP.

7. The process in claim 1 carried out in a continuously stirred tank reactor.

8. The process of claim 5 wherein the concentration of $H_2SO_4$ is from about 5% to about 20% by weight of the clay.

* * * * *